(12) United States Patent
Mannion et al.

(10) Patent No.: US 11,684,443 B2
(45) Date of Patent: Jun. 27, 2023

(54) SYSTEM AND METHOD FOR PACKAGING AND PREPARING A RADIOFREQUENCY ABLATION KIT

(71) Applicant: Avent, Inc., Alpharetta, GA (US)

(72) Inventors: Gavin H. Mannion, Atlanta, GA (US); Brett C. Leard, Seneca, SC (US); Ruoya Wang, Decatur, GA (US); Ryan D. Smith, Atlanta, GA (US); Mark R. Ellswood, Alpharetta, GA (US); Khoa T. Lien, Alpharetta, GA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 17/138,117

(22) Filed: Dec. 30, 2020

(65) Prior Publication Data

US 2022/0202520 A1 Jun. 30, 2022

(51) Int. Cl.
*A61B 50/33* (2016.01)
*A61B 50/00* (2016.01)
*A61B 50/30* (2016.01)

(52) U.S. Cl.
CPC ........ *A61B 50/33* (2016.02); *A61B 2050/005* (2016.02); *A61B 2050/3007* (2016.02); *A61B 2050/314* (2016.02)

(58) Field of Classification Search
CPC .............. A61B 50/33; A61B 2050/005; A61B 2050/3007; A61B 2050/314
USPC ................ 206/370, 570, 571, 363; 220/23.88
See application file for complete search history.

(56) References Cited

U.S. PATENT DOCUMENTS

| 5,144,942 A | | 9/1992 | Decarie et al. |
| 5,271,495 A | * | 12/1993 | Alpern ............. A61B 17/06133 |
| | | | 206/380 |
| 5,392,917 A | * | 2/1995 | Alpern ............... B65D 77/2056 |
| | | | 206/370 |
| 5,447,231 A | | 9/1995 | Kastenhofer |
| 5,833,057 A | * | 11/1998 | Char ...................... B65D 81/26 |
| | | | 229/148 |
| 5,996,798 A | * | 12/1999 | Gessert ................ B65D 81/052 |
| | | | 206/521 |

(Continued)

FOREIGN PATENT DOCUMENTS

EP  0602965 A2  6/1994

OTHER PUBLICATIONS

International Search Report and Written Opinion, dated May 6, 2022, received in connection with corresponding International Patent Application No. PCT/US2021/065616.

*Primary Examiner* — Steven A. Reynolds
(74) *Attorney, Agent, or Firm* — Meunier Carlin & Curfman LLC

(57) ABSTRACT

A system for packaging a kit for a radiofrequency ablation procedure protects a radiofrequency ablation kit without compromising its sterile barrier system through the hazards of handling, distribution, and storage. The system includes: an introducer tray configured to hold at least one introducer; a probe tray configured to hold at least one radiofrequency ablation probe; an outer carrier tray, a pouch configured to hold a tubing kit; and a dispenser carton. The introducer tray and the probe tray are held within the outer carrier tray, and the outer carrier tray and the pouch are configured to be held within the dispenser carton. A method of packaging a radiofrequency ablation kit is further described.

20 Claims, 11 Drawing Sheets

(56) References Cited

U.S. PATENT DOCUMENTS

| | | | | |
|---|---|---|---|---|
| 6,012,586 A | * | 1/2000 | Misra | A61B 50/30 |
| | | | | 206/370 |
| 7,972,255 B2 | * | 7/2011 | Inaba | B65D 75/008 |
| | | | | 206/524.1 |
| 8,342,335 B2 | * | 1/2013 | Couture | B65D 25/54 |
| | | | | 206/774 |
| 8,752,701 B2 | * | 6/2014 | Jacobs | A61N 5/1027 |
| | | | | 206/370 |
| D775,967 S | | 1/2017 | Lien | |
| 2002/0112981 A1 | * | 8/2002 | Cooper | A61B 90/94 |
| | | | | 206/570 |
| 2002/0185406 A1 | * | 12/2002 | Massengale | A61M 5/002 |
| | | | | 206/570 |
| 2003/0159966 A1 | | 8/2003 | McMichael et al. | |
| 2012/0053406 A1 | | 3/2012 | Conlon et al. | |
| 2014/0188001 A1 | | 7/2014 | Miller et al. | |
| 2015/0076023 A1 | * | 3/2015 | Kinyon | B65D 51/00 |
| | | | | 206/438 |
| 2015/0274410 A1 | * | 10/2015 | Tuet | H01M 8/2465 |
| | | | | 414/811 |

\* cited by examiner

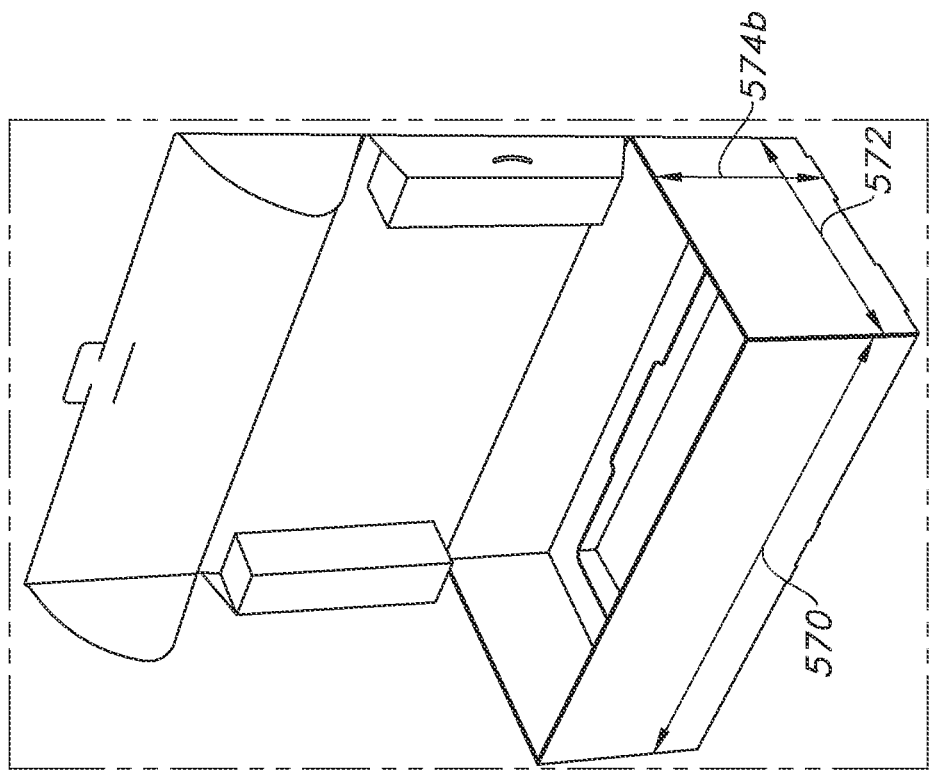
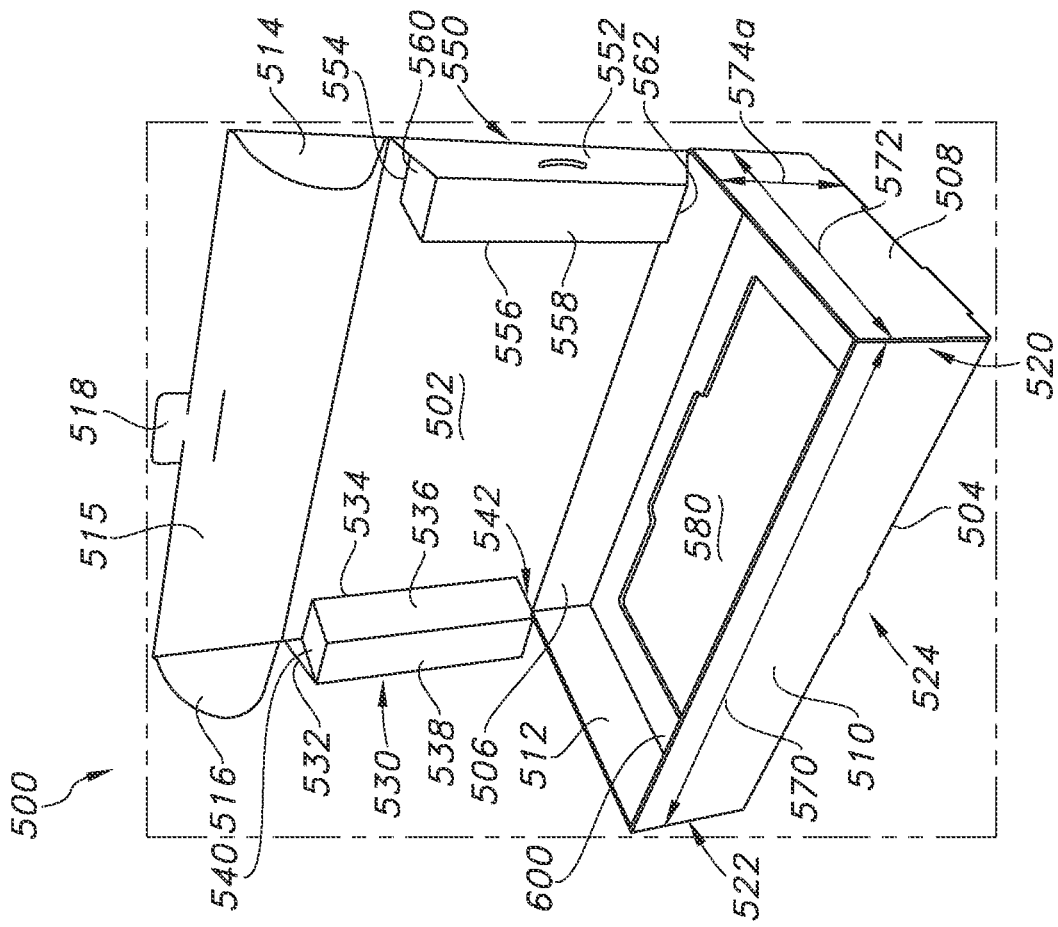
FIG. 15A
FIG. 15B

SYSTEM AND METHOD FOR PACKAGING AND PREPARING A RADIOFREQUENCY ABLATION KIT

FIELD OF THE INVENTION

The subject matter of the present invention relates generally to a packaging system and method for a radiofrequency ablation procedure kit.

BACKGROUND

Packaging systems for terminally sterilized medical devices can experience numerous hazards and challenges in the healthcare supply chain. Often times, the performance of a medical device packaging system may be sub-optimal. Moreover, varying conditions of climate, environment, and different modes of transportation further exacerbate the challenges faced in developing a medical device packaging system. These factors can contribute to the failure of a medical device packaging system to maintain sterility. ISO 11607-1:2019 sets the industry standard for packaging for terminally sterilized medical devices, including the requirements for materials, sterile barrier systems and packaging systems. However, due to the challenges described above, sub-optimal performance of medical device packaging systems can lead to non-compliance with the ISO 11607 industry standards. When the packaging materials do not effectively contain the contents of the packaging, i.e., the medical device(s), the sterile barrier system and/or the functionality of the medical device(s) may be compromised due to the hazards of handling, distribution and storage of the package. Non-compliance with these industry standards resulting in failure to meet sterility requirements or physical damage to the medical device(s) can lead to dissatisfied customers and loss of revenue.

Radiofrequency ablation treatment uses one or more electrodes housed in probes to deliver high-frequency electrical current, i.e., radiofrequency energy, to a patient's tissue as a treatment for chronic pain. In a cooled radiofrequency ablation treatment, cooled fluid is circulated within the probe(s) to reduce the temperature of the electrode-tissue interface so that more power can be applied to the target tissue without causing an unwanted increase in local tissue temperature that can result in tissue desiccation, charring, or steam formation. In a cooled radiofrequency ablation treatment, the probe(s) each include an electrical connection, e.g., an electrical cable, and one or more fluid connections, e.g., a fluid delivery tube and a fluid return tube, extending from the probe, that can be provided in the form of a cable-tubing assembly. The probe may be inserted into the patient's tissue via a probe introducer. Existing packaging for a radiofrequency ablation kit includes all components within a single sealed container or tray. The container can include a lid that is peeled off to access all of the components, and the peeling of the lid breaks the sterile barrier of the container. However, certain items of the radiofrequency ablation kit need to be set up at different times during a procedure. Thus, with the existing packaging systems, there is either a delay in the radiofrequency ablation procedure (due to not being able to open the package and set up certain items in advance), or the sterility of the components may be compromised (due to opening the package and setting up some components prior to the time of using the remaining components).

Consequently, there is a need for a packaging system and method for a radiofrequency ablation kit that accomplishes the unique goals of medical packaging, i.e., that allows sterilization, provides physical protection, maintains sterility up to point of use and allows aseptic presentation of the radiofrequency ablation kit. In particular, an agile packaging system with the ability to be dimensionally modified based on various configurations of the radiofrequency ablation kit would also be useful.

SUMMARY

Objects and advantages of the invention will be set forth in part in the following description, or may be obvious from the description, or may be learned through practice of the invention.

The present invention is directed to a system for packaging a kit for a radiofrequency ablation procedure. The system includes: an introducer tray configured to hold at least one introducer; a probe tray configured to hold at least one radiofrequency ablation probe; and an outer carrier tray, wherein the introducer tray and the probe tray are held within the outer carrier tray. The system further includes a pouch configured to hold a tubing kit. The system additionally includes a dispenser carton, wherein the outer carrier tray and the pouch are configured to be held within the dispenser carton.

In one particular embodiment, the introducer tray can be configured to nest within the probe tray.

In another embodiment, the system can further include a second probe tray configured to hold at least a second radiofrequency ablation probe. Further, the at least one radiofrequency ablation probe can include two radiofrequency ablation probes. Moreover, the second probe tray can be configured to stack with the probe tray. Further, the introducer tray can be configured to nest within the probe tray or the second probe tray.

In an additional embodiment, the outer carrier tray can include a lid formed from high density polyethylene fibers, wherein the lid is configured to seal the outer carrier tray to form a sterile barrier. Further, the contents of the outer carrier tray can be configured to be terminally sterilized after the outer carrier tray is sealed by the lid.

In yet another embodiment, the pouch can include a first material comprising high density polyethylene and a second material comprising a low density polyethylene film. Further, the pouch can be sealed, further wherein the contents of the pouch can be configured to be terminally sterilized after the pouch is sealed.

In a further embodiment, the dispenser carton can include a dispenser carton insert configured to minimize movement of the outer carrier tray and the pouch within the dispenser carton.

In still another embodiment, the system can further include a case configured to hold a plurality of dispenser cartons, wherein the case can be formed from knocked-down flat (KDF) corrugate material.

In one more embodiment, the dispenser carton can be made from paperboard.

In an additional embodiment, the probe tray, the introducer tray, and the outer carrier tray can each be thermoformed trays. Further, the thermoformed trays can be formed from polyethylene terephthalate glycol.

In another embodiment, the system can further include one or more paperboard sleeves configured to protect the at least one radiofrequency ablation probe.

The present invention is further directed to a method for packaging a kit for a radiofrequency ablation procedure. The method includes steps of:

providing the kit for a radiofrequency ablation procedure, the kit comprising at least one radiofrequency ablation probe, at least one introducer, and a tubing assembly;

inserting and securing the at least one radiofrequency ablation probe into a probe tray;

inserting and securing the at least one introducer into an introducer tray;

stacking the probe tray and the introducer tray and inserting the stacked probe tray and introducer tray into an outer carrier tray;

sealing the outer carrier tray; inserting the tubing assembly into a pouch; and inserting the outer carrier tray and the pouch into a dispenser carton.

In one particular embodiment of the method, the step of sealing the outer carrier tray can include sealing the outer carrier tray with a lid comprised of high density polyethylene fibers. Further, the method can further include a step of terminally sterilizing the contents of the outer carrier tray after sealing the outer carrier tray.

In another embodiment, the method can further include steps of: providing a dispenser carton insert, wherein the dispenser carton insert is inserted into the dispenser carton and configured to minimize movement of the outer carrier tray and the pouch within the dispenser carton.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 15A illustrates a perspective view of a dispenser carton for a probe kit including one to two probes according to an embodiment of the present invention;

FIG. 15B illustrates a perspective view of a dispenser carton for a probe kit including three to four probes according to an embodiment of the present invention;

DETAILED DESCRIPTION

Figures 1, 2, 3:
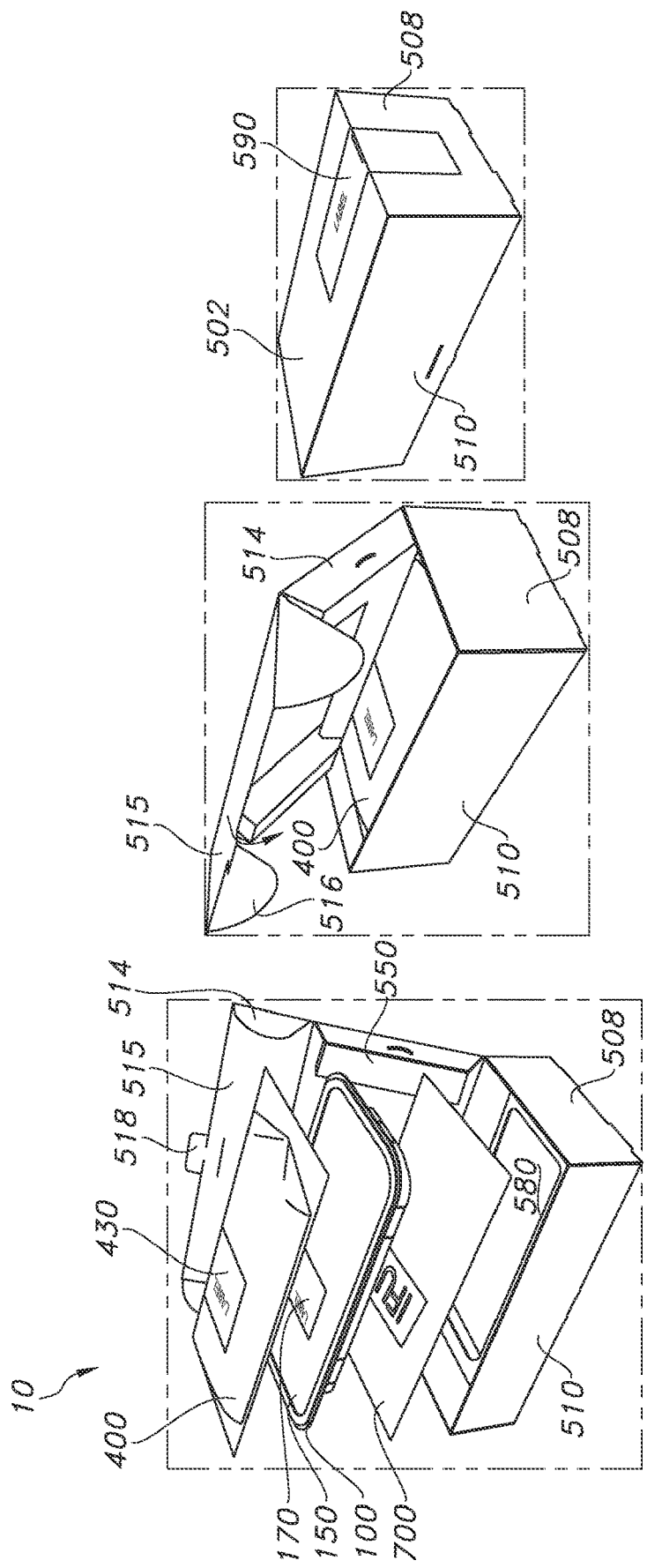
FIG. 1 illustrates an exploded perspective view of a system for packaging a radiofrequency ablation kit according to one particular embodiment of the present invention.
FIG. 2 illustrates a perspective view of the system of FIG. 1 with the radiofrequency ablation kit placed within a dispenser carton.
FIG. 3 illustrates a perspective view of the dispenser carton of FIGS. 1-2 in a closed configuration.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

Generally speaking, the present invention is directed to a system for packaging a kit for a radiofrequency ablation procedure protects a radiofrequency ablation kit. The system includes: an introducer tray configured to hold at least one introducer; a probe tray configured to hold at least one radiofrequency ablation probe; an outer carrier tray, a pouch configured to hold a tubing kit; and a dispenser carton. The introducer tray and the probe tray are held within the outer carrier tray, and the outer carrier tray and the pouch are configured to be held within the dispenser carton. The present invention is further directed to a method of packaging a radiofrequency ablation kit. The present inventors have found that the system and method of the present invention effectively contains the kit for a radiofrequency ablation without compromising the sterile barrier system or functionality of the kit through the hazards of handling, distribution and storage. The specific features of the system and method of the present invention may be better understood with reference to FIGS. 1-17.

Referring now to FIG. 1, one embodiment of system 10 for packaging a kit for a radiofrequency ablation procedure is shown. The system 10 includes an outer carrier tray 100 that contains an introducer tray 300 (see FIG. 4) and a probe tray 200 (see FIG. 4), a pouch 400 configured to hold a tubing kit 40, and a dispenser carton 500. As will be described in further detail below and with reference to FIGS. 4-5, 6A-B and 9, the introducer tray 300 is configured to hold one or more introducers 30 of the radiofrequency ablation kit, and the probe tray 200 is configured to hold one or more radiofrequency probe assemblies 20 of the radiofrequency ablation kit. Optionally, the system 10 may additionally include an Instructions for Use (IFU) booklet 700 and/or a Quick Reference Guide (QRG) booklet. The outer carrier tray 100 and pouch 400 are configured to be inserted within the dispenser carton 500, e.g., within the open space 580 as shown in FIGS. 1 and 2, such that the dispenser carton 500 can be closed for transport and storage of the kit for a radiofrequency ablation procedure, as shown in FIG. 3. The system 10 may also include a carton or case 800 (see FIG. 15) in which a plurality of dispenser cartons 500 can be transported and stored.

Figure 5:
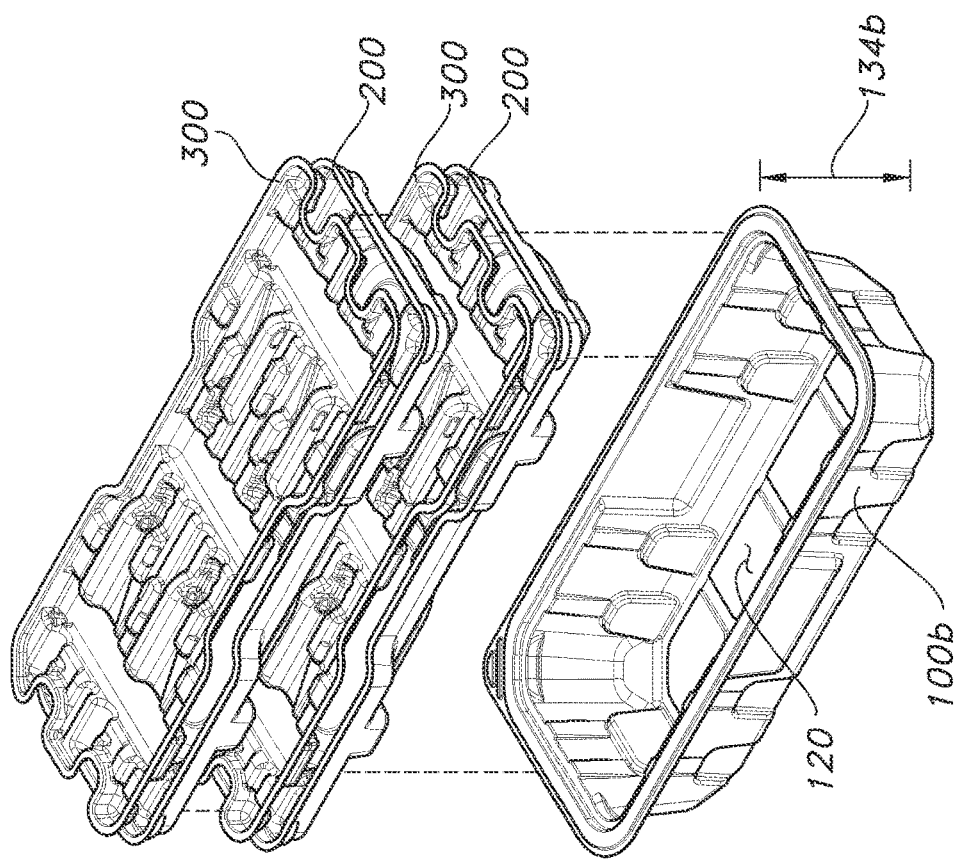
FIG. 5 illustrates an exploded perspective view of a radiofrequency ablation kit configured for three or four radiofrequency ablation probes.
Figure 4:
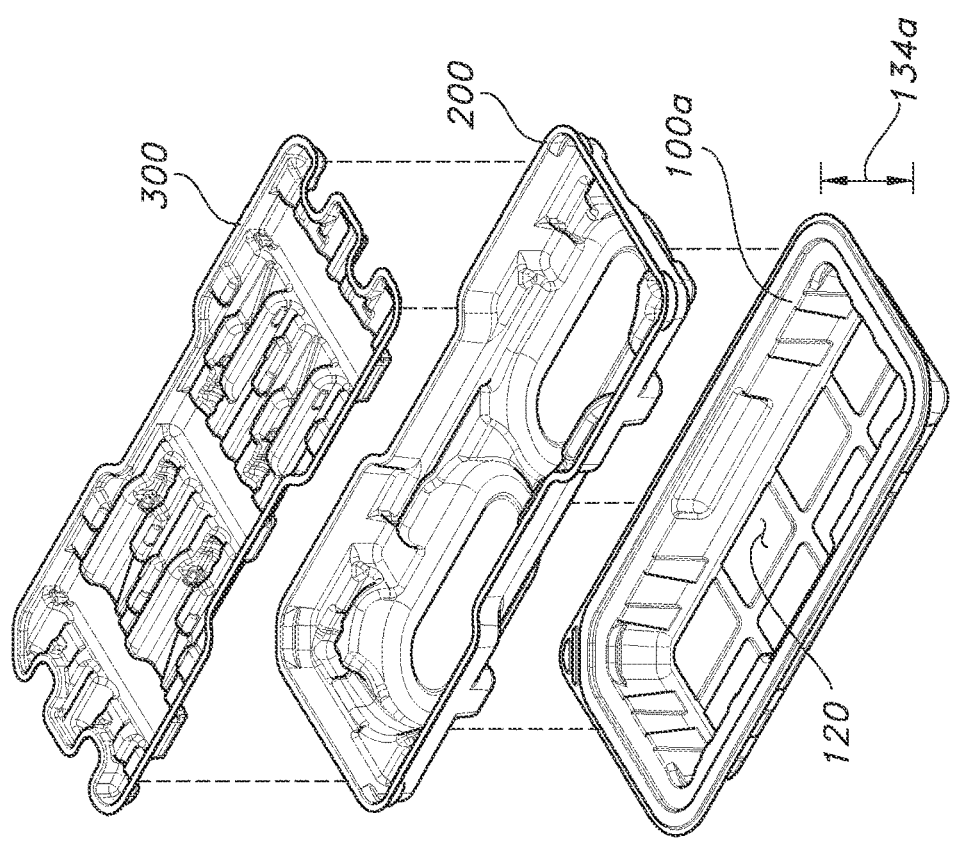
FIG. 4 illustrates an exploded perspective view of a radiofrequency ablation kit configured for one or two radiofrequency ablation probes.

Turning now to FIGS. 4-9, the probe tray 200, introducer tray 300 and outer carrier tray 100 will be described in further detail. Each introducer tray 300 is configured to rest above a probe tray 200, which all may be inserted within an outer carrier tray 100. For instance, the introducer tray 300 may be seated in/on the probe tray 200, as shown in FIGS. 4 and 5. FIG. 4 illustrates a carrier tray 100a configured to hold one probe tray 200 and introducer tray 300, wherein the carrier tray 100a has a height 134a. In contrast, FIG. 5 illustrates a carrier tray 100b configured to hold two probe trays 200 and two introducer trays 300, wherein the carrier tray 100b has a height 134b. The height 134b of the carrier tray 100b is longer than the height 134a of the carrier tray 100a. As shown in FIG. 5, each respective probe tray 200 and introducer tray 300 are stacked together, and each assembly of a probe tray 200 and introducer tray 300 can be stacked on top of each other and inserted within the open portion 120 of the tray 100b.

Figure 6A:
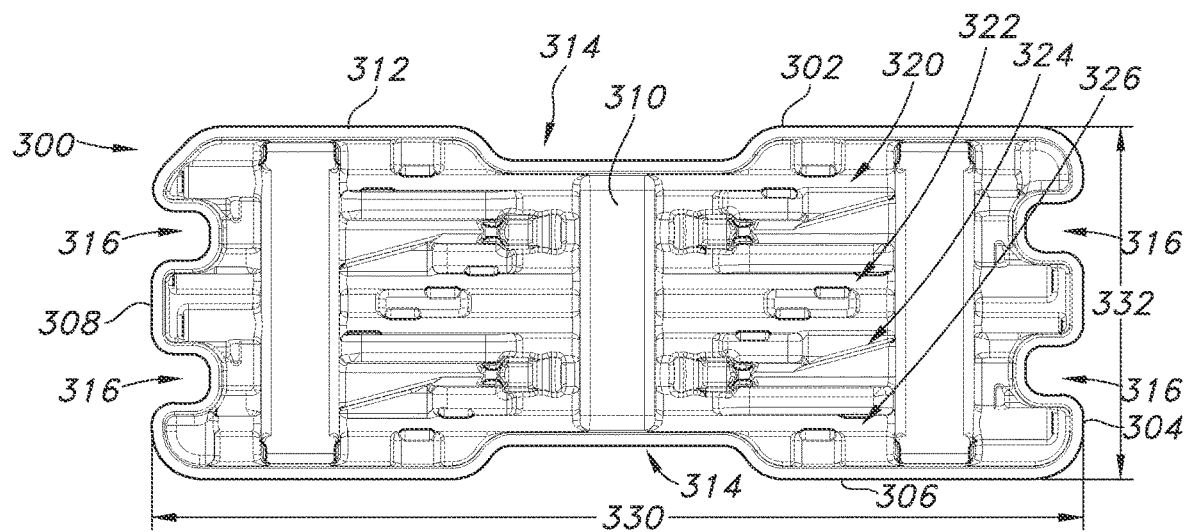
FIG. 6A illustrates a top view of an introducer tray of the radiofrequency ablation kit of FIG. 4.
Figure 6B:
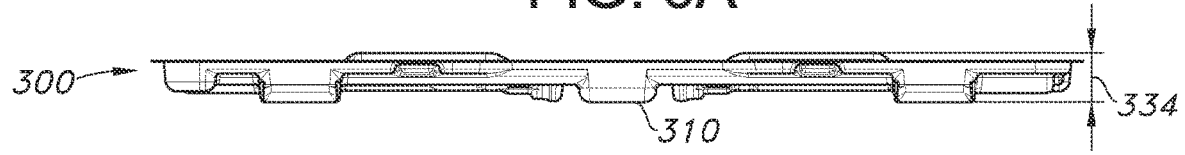
FIG. 6B illustrates a side view of an introducer tray of the radiofrequency ablation kit of FIG. 4.

The introducer tray 300 is illustrated in further detail in FIGS. 6A-B. The introducer tray 300 has a first side 302, a second side 304, a third side 306 and a fourth side 308. The introducer tray has a lower surface 310 that terminates at each of the four sides 302, 304, 306, 308, upon which one or more introducers 30 are configured to be received or held in place. The introducer tray 300 further includes a flange 312 extending around the sides 302, 304, 306, 308. The first side 302 includes an indented portion 314 disposed between the second side 304 and fourth side 308. The third side 304 additionally includes an indented portion 314 disposed between the second side 304 and the fourth side 308. As shown in FIG. 6A, the indented portions 314 of the first side 302 and third side 306 can match or mirror each other. For instance, the indented portions 314 may be disposed in a center portion of the tray 300 such that the indented portions 314 function as a gripping feature for picking up the introducer tray 300. The second side 304 and the fourth side 308 may each include one or more indented portions 316, such as U-shaped indented portions 316 shown in FIG. 6A. For instance, each of the second side 304 and fourth side 308 may include two indented portions 316. The indented portions 316 may be disposed between the first side 302 and the third side 306 of the introducer tray 300. The indented portions 316 may function as gripping or lifting features for lifting the introducer tray 300 from the probe tray 200 when the introducer tray 300 and probe tray 200 are coupled together as shown in FIGS. 4 and 5.

The lower surface 310 of the introducer tray 300 includes at least one indentation configured to receive an introducer 30. For instance, the introducer tray 300 may include a first introducer indent 320, a second introducer indent 322, a third introducer indent 324, and a fourth introducer indent 326 such that the introducer tray 300 can hold up to four introducers 30.

The introducer tray 300 may have a length 330 extending from the second side 304 to the fourth side 308, a width 332 extending from the first side 302 to the third side 306, and a height 334 extending from the lower surface 310 to the flange 312 (see FIG. 6B). The length 330 can be in a range from about 11 inches to about 14 inches, such as from about 12 inches to about 13 inches, for example in one embodiment the length 230 can be about 12.72 inches. The width 332 can be in a range from about 3 inches to about 6 inches, such as from about 4 inches to about 5 inches, e.g., in one embodiment the width 332 is about 4.82 inches. The height 334 can be in a range from about 0.4 inches to about 1 inch, such as from about 0.5 inches to about 0.75 inches, for example in one embodiment the height 234 is about 0.675 inches.

Figure 7A:
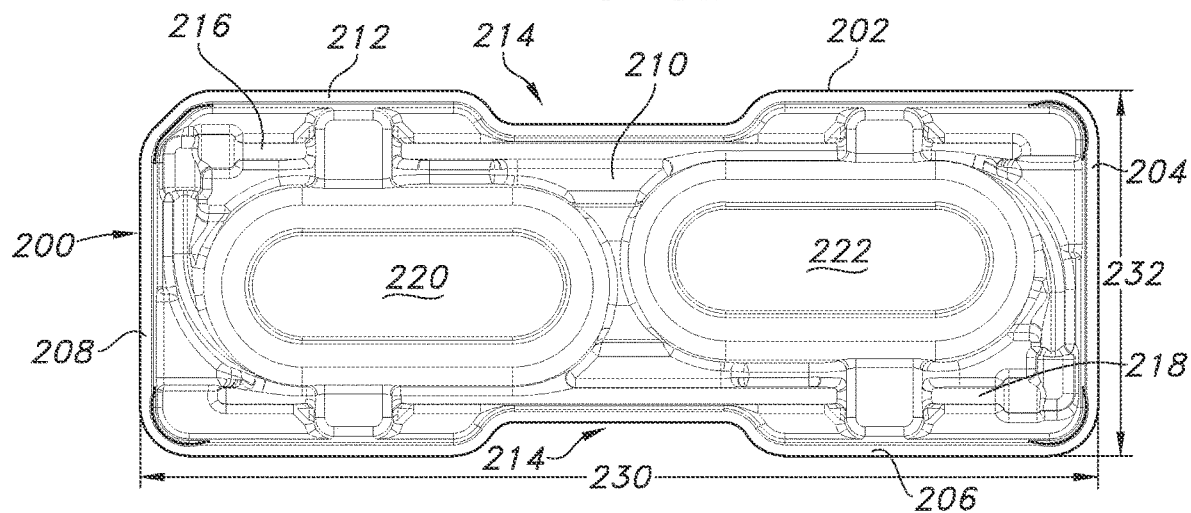
FIG. 7A illustrates a top view of a probe tray of the radiofrequency ablation kit of FIG. 4.
Figure 7B:
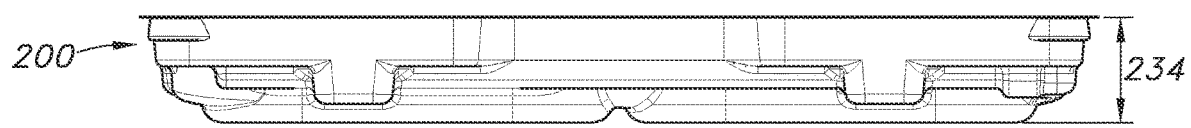
FIG. 7B illustrates a side view of a probe tray of the radiofrequency ablation kit of FIG. 4.

The probe tray 200 is illustrated in further detail in FIGS. 7A-B. The probe tray 200 has a first side 202, a second side 204, a third side 206 and a fourth side 208. The probe tray 200 has a lower surface 210 that terminates at each of the four sides 202, 204, 206, 208, upon which one or more probe assemblies 20 configured to be received or held in place. The probe tray 200 further includes a flange 212 extending around the sides 202, 204, 206, 208. The first side 202 includes an indented portion 214 disposed between the second side 204 and fourth side 208. The third side 206 additionally includes an indented portion 214 disposed between the second side 204 and the fourth side 208. As shown in FIG. 7A, the indented portions 214 of the first side 202 and third side 206 can match or mirror each other. For instance, the indented portions 214 may be disposed in a center portion of the tray 200 such that the indented portions 214 function as a gripping feature for picking up the probe tray 200, e.g., removing the probe tray 200 from the carton 100 as shown in FIGS. 4 and 5.

The lower surface 210 of the probe tray 200 can include indented portions configured for receiving the components of the probe assembly 20. As shown in FIG. 7A, the lower surface 210 can include a first probe indent 216 for receiving a first probe 26 and a second probe indent 218 for receiving a second probe 26, such that the probe tray 200 can receive and hold up to two probe assemblies. The lower surface 210 may further include one or more indentations for holding the cable/tubing 24 of each probe assembly 20, e.g., a first tubing indent 220 and a second tube indent 222 as shown in FIG. 7A.

The probe tray 200 may have a length 230 extending from the second side 204 to the fourth side 208, a width 232 extending from the first side 202 to the third side 206, and a height 234 extending from the lower surface 210 to the flange 212 (see FIG. 76). The length 230 and width 232 are configured to be longer than the length 330 and width 332 of the introducer tray 300 such that the introducer tray 300 can be nested in the probe tray 300. The length 230 can be in a range from about 11 inches to about 14 inches, such as from about 12 inches to about 13 inches, for example in one embodiment the length 230 can be about 12.78 inches. The width 232 can be in a range from about 3 inches to about 6 inches, such as from about 4 inches to about 5 inches, e.g., in one embodiment the width 232 is about 4.88 inches. The height 234 can be in a range from about 1 inch to about 2 inches, such as from about 1.25 inches to about 1.75 inches, for example in one embodiment the height 234 is about 1.42 inches.

Figure 8:
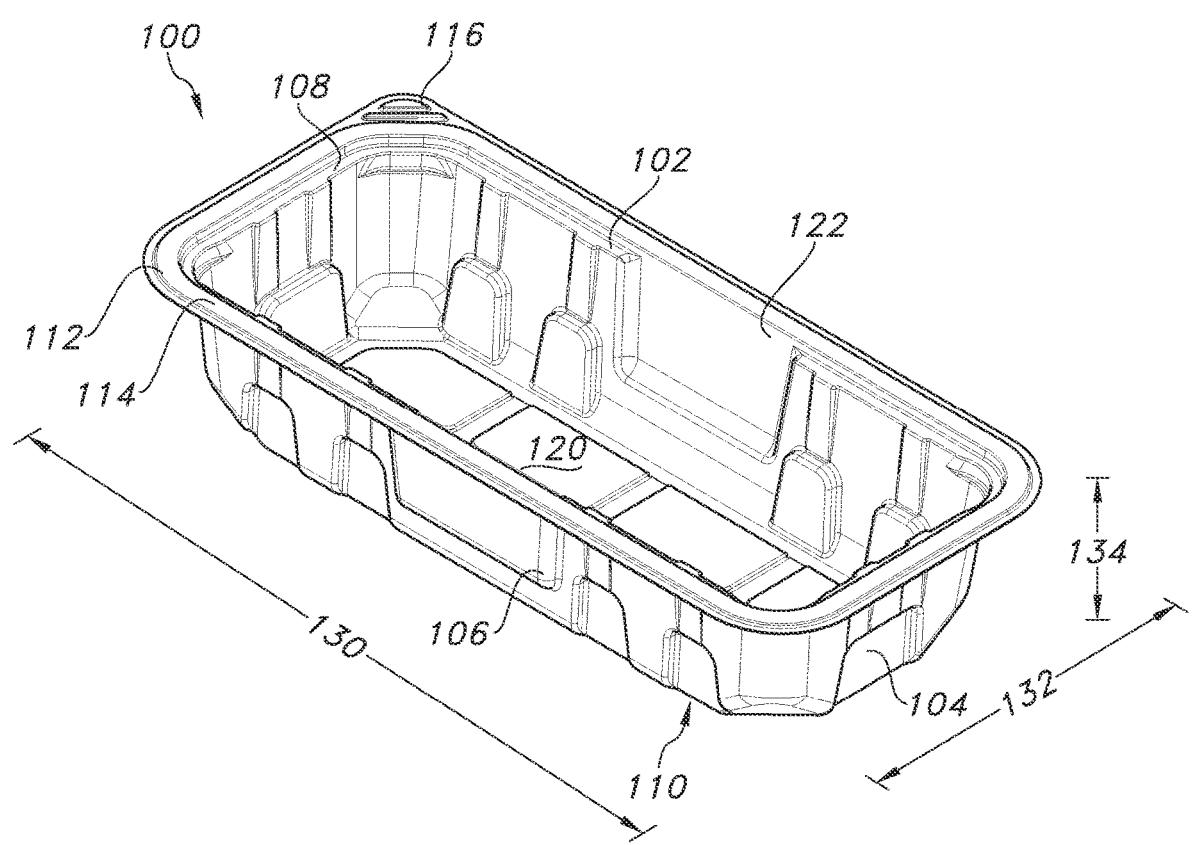
FIG. 8 illustrates a perspective view of an outer carrier tray of the radiofrequency ablation kit of FIG. 4.

As shown in FIG. 8, the system 10 further includes an outer carrier tray 100 that is configured to contain the probe tray 200 and introducer tray 300. In particular, the outer carrier tray 100 is configured to contain an introducer tray 300 nested within a probe tray 200. The outer carrier tray 100 includes a first side 102, a second side 104, a third side 106, a fourth side 108, and a lower surface 110 surrounded by the first side 102, second side 104, third side 106 and fourth side 108. An open portion 120 is formed between the first side 102, second side 104, third side 106 and fourth side 108 as walls and the lower surface 110 as a floor. Additionally, the outer carrier tray 100 includes a flange 112 extending from an upper end of the first side 102, second side 104, third side 106 and fourth side 108. The flange 112 includes a sealing surface 114. The flange 112 can further include at least one holding portion 116 extending from a corner of the flange 112, e.g., at a corner between the first side 102 and second side 104, second side 104 and third side 106, third side 106 and fourth side 108, or the first side 102 and the fourth side 108 as shown in FIG. 8. The outer carrier tray 110 has a length 130 extending from the second side 104 to the fourth side 108, a width 132 extending from the first side 102 to the third side 106, and a height 134 that extends between the lower surface 110 and the flange 112. The length 130 can be in a range from about 13 inches to about 16 inches, such as from about 14 inches to about 15 inches, for example in one embodiment the length 130 can be about 14.85 inches. The width 132 can be in a range from about 5 inches to about 8 inches, such as from about 6 inches to about 7 inches, for example in one embodiment the width 132 can be about 6.95 inches. The height 134 may be a first height 134a when the outer carrier tray 100 is configured to hold 1-2 probes in a single probe tray 200, as shown in FIG. 4, or a second height 134b when the outer carrier tray 100 is configured to hold 3-4 probes in two probe trays 200 stacked on top of each other, as shown in FIG. 5. For instance, the height 134a can be in a range from about 1 inch to about 2 inches, e.g., about 1.65 inches. The height 134b can be in a range from about 3 inches to about 4 inches, e.g., about 3.15 inches.

Additionally, one or more of the sides can include a depression 122 configured to provide space for a user's hand to reach inside the outer carrier tray 100 to remove contents from the outer carrier tray 100. For instance, the first side 102 and the third side 106 may each include a depression 122. The depression 122 may be generally centrally positioned between the second side 104 and the fourth side 108, as shown in FIG. 8. As illustrated in FIGS. 4-5, the depressions 122 can be aligned with the indentations 214 of the probe tray 200 and indentations 314 of the introducer tray 300, such that a user may reach into the space formed between the indentations 214, 314 and the depressions 122 and grasp the introducer tray 300 and probe tray 200 to remove the introducer tray 300 and probe tray 200 from the open portion 120 of the outer carrier tray 100.

Figure 9:
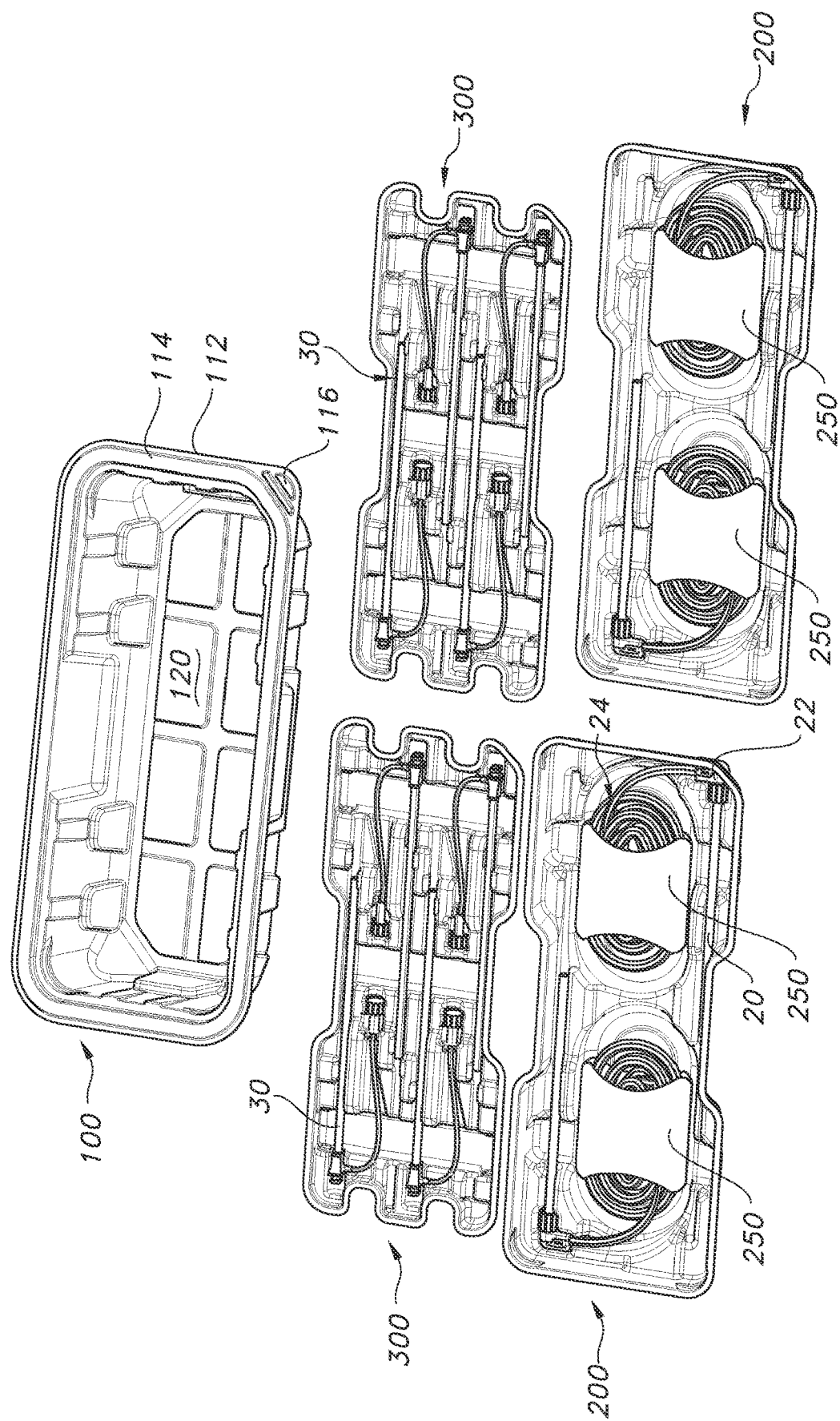
FIG. 9 illustrates an exploded view of the radiofrequency ablation kit of FIG. 5 including radiofrequency probes and introducers.

FIG. 9 illustrates an outer carrier tray 100, and a pair of introducer trays 300 and probe trays 200 each containing their respective contents of a probe kit. Specifically, the introducer trays 300 of FIG. 9 each contain a plurality of introducers 30. The probe trays 200 of FIG. 9 each contain two sets of: a probe 20 attached to a probe handle 22 and a cable-tubing assembly 24. Each cable-tubing assembly 24 is contained within a probe sleeve 250, which will be described in further detail below.

Returning briefly to FIG. 1, the outer carrier tray 100 may include a lid 150 to enclose the open portion 120 of the outer carrier tray 100. The lid 150 can be sealed to the sealing surface 114 of the flange 112 of the outer carrier tray 100. Optionally, as shown in FIG. 1, a label 170 can be adhered to the lid 150 of the outer carrier tray 100. The lid 150 may provide a sterile barrier configured to enable sterilization of the contents of the outer carrier tray 100 and maintain the sterility after sterilization. The lid 150 can be made from a material that is not affected by climatic changes in humidity, temperature, or atmospheric pressure. The lid 150 can be formed from a sheet of filter or sterilization material, and can be made from a number of materials and, generally, may be disposable in that the lid 150 can be a one-use item that is discarded or recycled after their initial use. Generally, disposable materials can include nonwoven materials made from either or both natural and synthetic fibers such as paper, fibrous polymeric nonwovens, and films (e.g., PTFE porous films or membranes), which are capable of passing sterilants and retarding transmission of bacteria and other contaminants.

Nonwoven sterilization materials present several advantages due to their barrier properties, economics, and consistent quality. The nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, nylon, polyesters, polyolefins, and many other materials. The fibers may be relatively short, staple length fibers, typically less than three inches, or longer and substantially more continuous fibers such as are produced by spunbonding and/or meltblowing processes. Whatever materials are chosen, the resultant sheet of filter material must be compatible with the particular sterilization technique being used and must also provide both strength and barrier properties to maintain the sterile nature of the contents of the outer carrier tray 100 until use. In the illustrated exemplary embodiment, shown in FIG. 1, the sheet of filter material forming the lid 150 can be a spunbond olefin film, e.g., high density polyethylene. For example, the lid 150 can be formed from a DuPont TYVEK material, such as TYVEK 1059B with CR90 coating.

Each of the outer carrier tray 100, the probe tray 200 and the introducer tray 300 may be formed from a thermoplastic material. For example, each of the trays 100, 200 and 300 may be formed from a polyester material, e.g., a polyethylene terephthalate (PET) material, such as polyethylene terephthalate glycol (PETG). Each of the trays 100, 200, 300 may have a thickness in a range from about 0.010 inches (0.25 mm) to about 0.050 inches (1.27 mm). For example, the outer carrier tray 100 may have a thickness of about 0.04 inches (about 1.02 mm), the probe tray 200 may have a thickness of about 0.025 inches (about 0.76 mm), and the introducer tray 300 may have a thickness of about 0.025 inches (about 0.064 mm). For instance, the relative thickness of each of the trays 100, 200, 300 may correspond with the relative sizes of each of the respective trays 100, 200, 300: the outer carrier tray 100 has larger dimensions (length, width, height) than the probe tray 200 and the introducer tray 300, which are configured to nest within the outer carrier tray 100, so the outer carrier tray 100 may correspondingly have a larger thickness of the tray material.

Figure 10A:
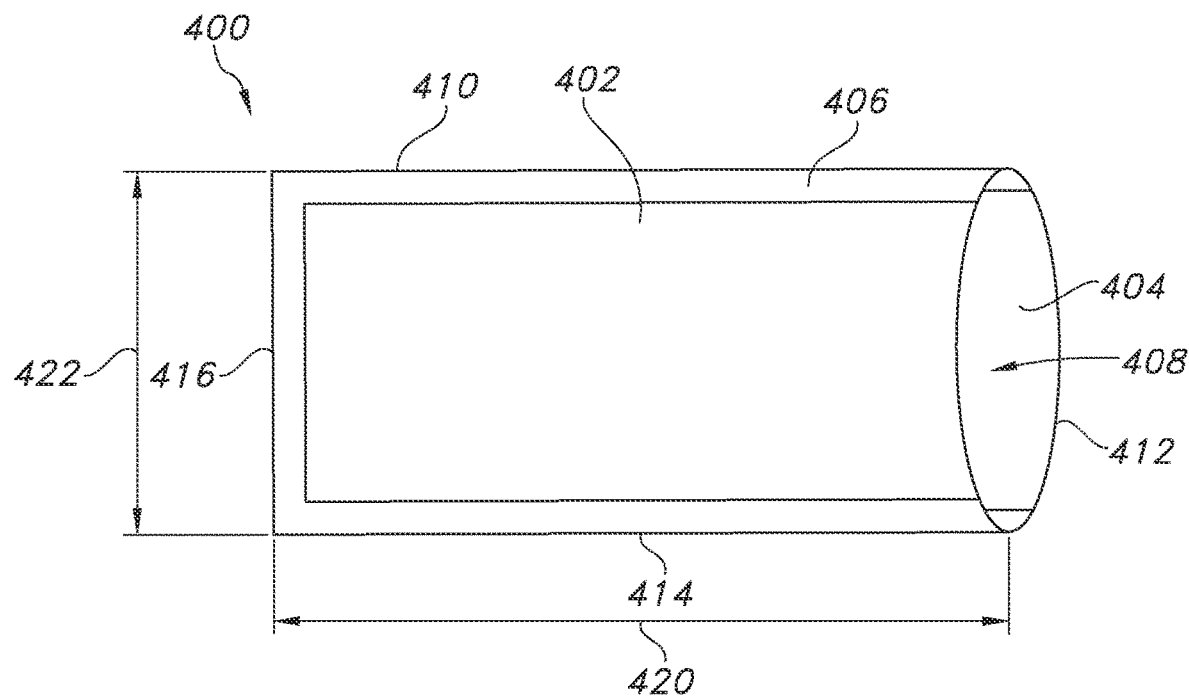
FIG. 10A illustrates a perspective view of a tubing pouch of the radiofrequency ablation kit of FIG. 1.
Figure 10B:
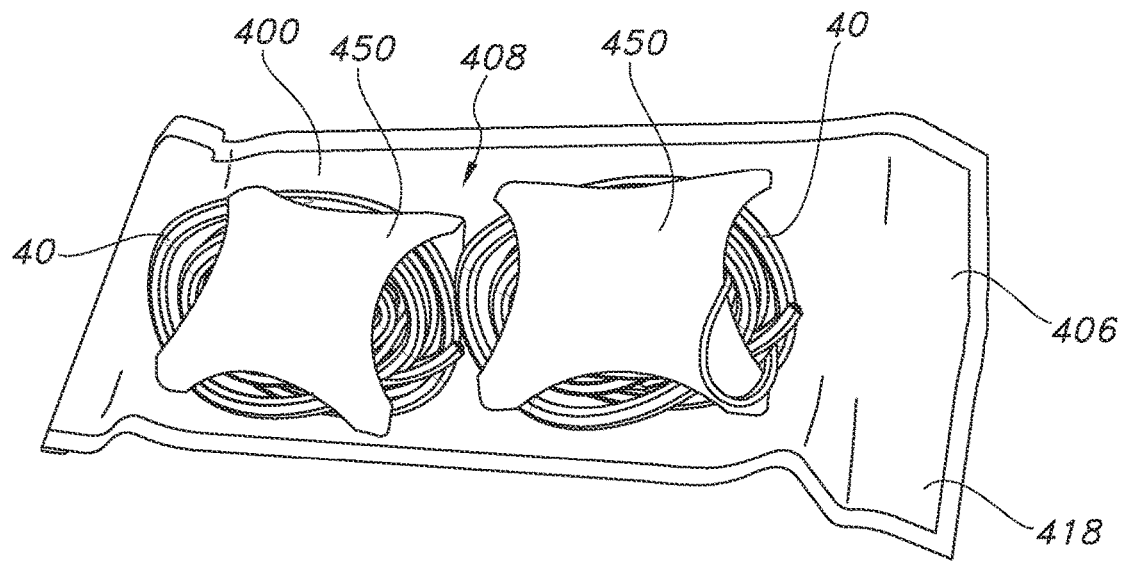
FIG. 10B illustrates a top view of the tubing pouch of FIG. 10A with the tubing kit enclosed within the tubing pouch.

Turning now to FIGS. 10A-B, the system 10 further includes a pouch 400 configured to hold a tubing kit 40. The pouch 400 has a first surface 402 and a second surface 404 opposite the first surface 402. The pouch 400 has a first side 410, second side 412, third side 414 and fourth side 416. A sealing flange 406 extends around the first side 410, second side 412, third side 414 and fourth side 416 to seal the first surface 402 to the second surface 404. The pouch 400 may optionally include a flange holding portion 418 at a corner of the pouch 400 that is configured to be used as a grasping portion for a user. Additionally, the flange holding portion 418 may form a point at which the first surface 402 and the second surface 404 can be separated. For instance, the first surface 402 and the second surface 404 may be sealed together around the entire sealing flange 406 except remaining un-attached at the flange holding portion 418. The pouch 400 further has an open portion 408 formed between the first surface 402 and the second surface 404, into which contents of the pouch 400 may be inserted such as one or more tubing kits 40 as shown in FIG. 10B.

The pouch 400 has a length 420 extending between the second side 412 and the fourth side 416, and a width 422 extending between the first side 410 and the third side 414. The length 420 can be in a range from about 10 inches to about 16 inches, such as from about 12 inches to about 16 inches, for example in one embodiment the length 420 may be about 15 inches. The width 422 can be in a range from about 5 inches to about 7 inches, for example about 6 inches.

As shown in FIG. 10B, the first surface 402 and the second surface 404 may be formed from different materials, or the first surface 402 and the second surface 404 may be formed from the same material. For example, as shown in FIG. 10B, the first surface 402 may be formed from a transparent or translucent material that enables visibility of the contents of the pouch 400. For example, the first surface 402 may be formed from a film. The film may be, for example, polyethylene terephthalate (PET), low density polyethylene (LDPE), and/or a combination thereof. The second surface 404 may be formed from a different material than the first surface 402, and may have a different level of opacity than the first surface 402, as shown in FIG. 10B. For example, the second surface 404 may be formed from a nonwoven sterilization material similar to or the same as the material used for the lid 150 of the outer carrier tray 100. In one particular embodiment, the second surface 404 may be formed from a high density polyethylene material such as uncoated DuPont TYVEK 1073B.

Figure 11:
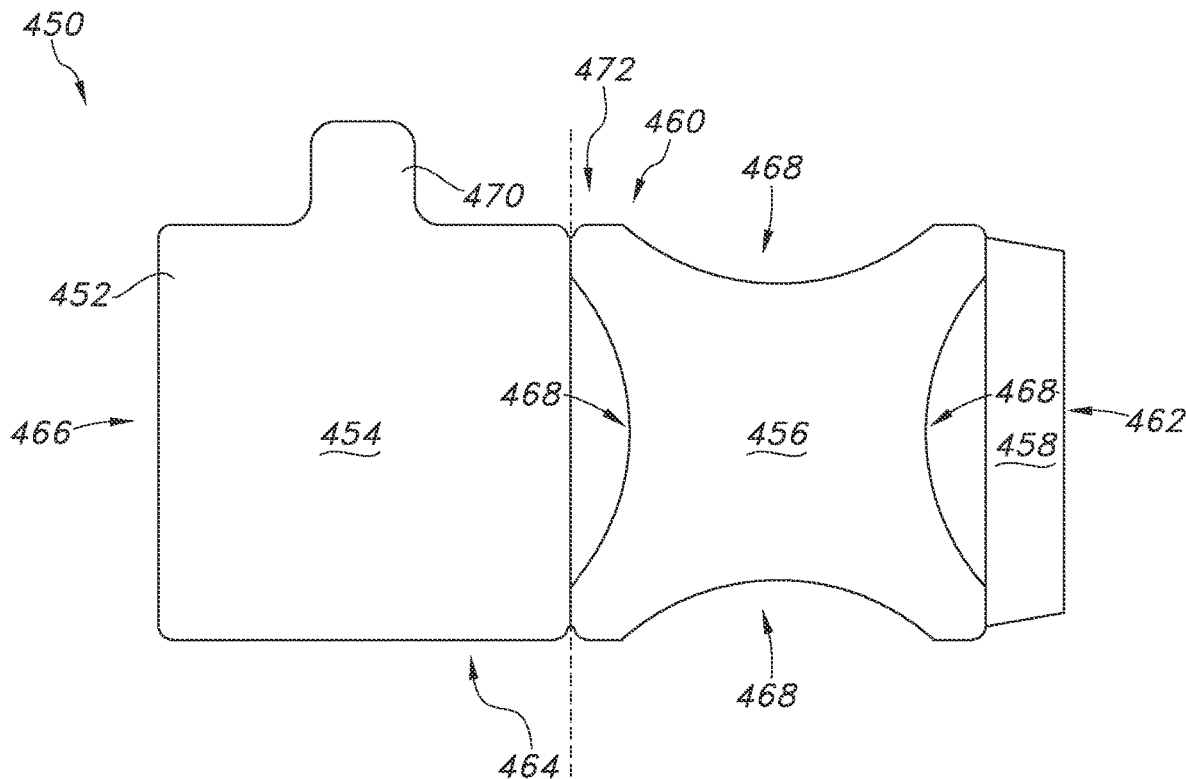
FIG. 11 illustrates a top view of a tubing sleeve according to an embodiment of the present invention.

Further shown in FIGS. 10B and 11, a tubing sleeve 450 may be provided for the tubing kit 40. The tubing sleeve 450 has a body 452 that is formed by a first panel 454, a second panel 456 opposite the first panel 454, and a third panel 458 in the form of a flap configured to secure the first panel 454 and the second panel 456. The tubing sleeve 450 has a first side 460, a second side 462, a third side 464 and a fourth side 466. The second panel 456 may include concave cutouts 468 along the first side 460, second side 462, third side 464 and fourth side 466, as shown in FIGS. 10B and 11, such that a tubing kit 40 coiled and inserted within the tubing sleeve 450 can extend through the concave cutouts 468. Additionally, as shown in FIG. 11, the tubing sleeve 450 may further include a holding tab 470. The holding tab 470 may extend from the first panel 454 such that the holding tab 470 does not interfere with the concave cutouts 468 of the second panel 456. The first panel 454, second panel 456 and third panel 458 of the tubing sleeve 450 may be formed from a single piece of material. The second panel 456 may be connected to the first panel 454 on one side and the flap 458 on an opposite side. When the single piece of material of the tubing sleeve 450 is folded along a fold line 472 extending between the first panel 454 and the second panel 456, the third panel 458 may be brought into contact with the fourth side 466 of the first panel 454. The third panel 458 or flap may be secured to the first panel 454 using any suitable means, such as adhesive.

Figure 12:
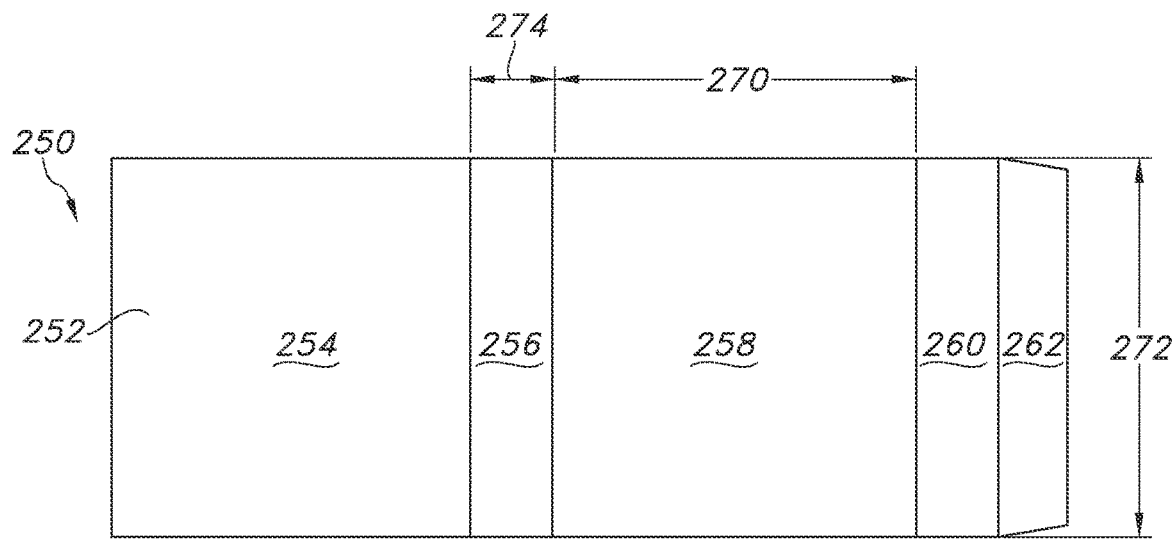
FIG. 12 illustrates a top view of a probe sleeve according to an embodiment of the present invention.

As illustrated in FIGS. 9 and 12, a probe sleeve 250 may be provided. The probe sleeve 250 can be configured to surround the probes 20 and the cables 24 within the probe tray 200. For instance, the probe sleeve 250 may ensure that the probe 20 and cable 24 have a secure fit within the probe tray 200, and further may be configured to keep the cable 24 intact without developing any rips, cuts, tears, or cracks, during packaging, shipment and storage. The probe sleeve 250 is formed from a body 252, which may be formed of unitary construction (i.e., formed from one piece of material). The body 252 may include a first panel 254, a second panel 256, a third panel 258, a fourth panel 260 and a fastening panel 262. The first panel 254, second panel 256, third panel 258 and fourth panel 260 may form the sides of a quadrilateral shape, such as a rectangular shape.

The probe sleeve 250 may have a length 270, a width 272 and a height 274. The length 270 may be generally equal to a length of both the first panel 254 and the third panel 258. For example, the length 270 may be in a range from about 2 inches (about 5 cm) to about 3 inches (about 7.6 cm), such as from about 2.25 inches (about 5.7 cm) to about 2.75 inches (about 7 cm), for instance, the length 270 may be about 2.625 inches (about 6.67 cm). The width 272 may be generally equal to a width of each of the panels 254, 256, 258 and 260 as shown in FIG. 12. For example, the width 272 may be in a range from about 2.25 inches (about 5.7 cm) to about 3.25 inches (about 8.25 cm), such as from about 2.5 inches (about 6.35 cm) to about 3 inches (about 7.6 cm), for example the width 272 may be about 2.75 inches (about 7 cm). The height 274 of the probe sleeve 250 may be generally equal to a length of both the second panel 256 and fourth panel 260. For example, the height 274 may be in a range from about 0.25 inches (about 0.64 cm) to about 0.75 inches (about 1.9 cm), such as from about 0.4 inches (about 1 cm) to about 0.7 inches (about 1.8 cm), for example the height 274 may be about 0.6 inches (about 1.5 cm).

In other words, the first panel 254 and third panel 258 may have generally equal size and shape, and the second panel 256 and fourth panel 260 may have generally equal size and shape, such that the probe sleeve 250 forms a rectangular shape when folded. The probe sleeve fastening panel 262 may extend from one end of the probe sleeve body 252, such as from the fourth panel 260 as shown in FIG. 12. The fastening panel 262 can be configured to be brought into contact with the first panel 254, e.g., by folding the body 252 between each of the respective panels 254, 256, 258, 260 and the fastening panel 262, and secured to the first panel 254 using any suitable means, such as adhesive.

Figure 13:
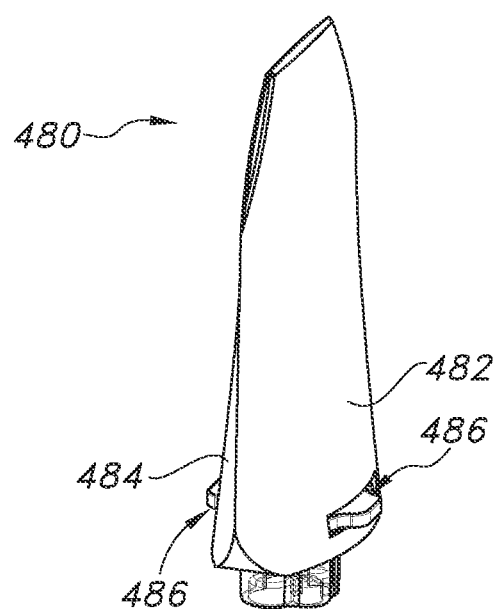
FIG. 13 illustrates a perspective view of an IV spike cover according to an embodiment of the present invention.

As illustrated in FIG. 13, an IV spike cover 480 may be provided. The IV spike cover 480 may include a first side 482 and a second side 484 configured to surround an IV spike (not shown). Additionally, the IV spike cover 480 can include one or more openings 486 on the first side 482 and/or the second side 484 configured to secure the IV spike within the IV spike cover 480.

Figure 14:
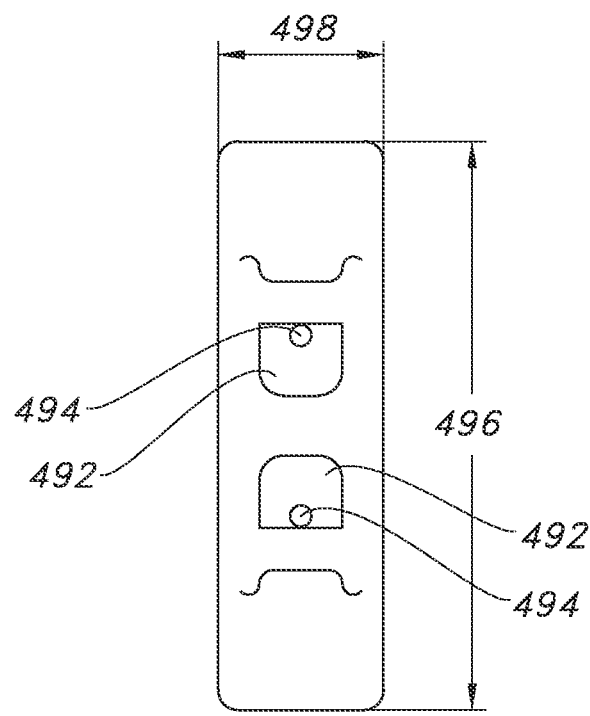
FIG. 14 illustrates a top view of an epsilon ruler card holder according to an embodiment of the present invention.

As illustrated in FIG. 14, an epsilon ruler card holder 490 may be provided to hold an epsilon ruler configured for use with the probe 20. The epsilon card holder 490 may be sized and shaped to fit within the introducer tray 300. For instance, the epsilon card holder 490 can have a length 496 in a range from about 2 inches to about 6 inches, such as about 3.5 inches, and a width 498 in a range from about 0.5 inches to about 1.5 inches, such as about 1 inch. The epsilon card holder 490 can include one or more flaps 492 configured to be folded to hold the epsilon ruler in place. For instance, the epsilon card holder 490 may have one or more openings 494 through which the epsilon ruler can be inserted such that the epsilon card holder 490 retains the epsilon ruler in place. The one or more openings 494 may be positioned on the foldable flaps 492, as shown in FIG. 14. By securing the epsilon ruler on the epsilon ruler card holder 490, the epsilon ruler can be prevented from becoming loose within the outer carrier tray 100. Additionally, securing the epsilon ruler on the epsilon ruler card holder 490 and placed within the introducer tray 300 can further protect the lid 150 of the outer carrier tray 100 from damage, thereby ensuring the presence of a sterile barrier and improving safety.

The tubing sleeve 450, the probe sleeve 250, the IV spike cover 480 and/or the epsilon ruler card holder 490 each may be constructed of any suitable material including paper-based materials such as, for example, carton cardboard stock, paperboard, heavy structural paper, container stock, corrugated paperboard, plastic coated paper, a plastic sheet, a wax-coated paper or the like, or a combination thereof. The paper-based material(s) can be provided as a single layer or multiple layers. In some aspects of the invention, the body 452 of the tubing sleeve 450, the body 252 of the probe sleeve 250, the IV spike cover 480 and the epsilon ruler card holder 490 are each formed from paperboard or fiberboard, in particular, solid bleached sulfate (SBS; also known as solid bleached board). The paper-based material(s) of each of the tubing sleeve 450, probe sleeve 250, the IV spike cover 480 and/or the epsilon ruler card holder 490 may have a thickness in a range from about 0.01 inches (about 0.25 mm) to about 0.03 inches (about 0.75 mm), for instance about 0.16 inches. The paper-based material(s) used may maintain aseptic handling of the tubing kit 400, probe 20 and/or the IV spike, respectively, and provide sufficient structural characteristics to form a secure cover for the tubing kit 400, probe 20 and IV spike as contemplated by the present invention. Moreover, the paper-based material(s) may be biodegradable such that the tubing sleeve 450, the probe sleeve 250, the IV spike cover 480 and/or the epsilon ruler card holder 490 of the present invention are more environmentally friendly than single-use polymer-based alternatives known in the art.

Turning now to the dispenser carton 500 as shown in FIGS. 1-3 and 15A, the dispenser carton 500 has an upper surface 502, a lower surface 504, a first side 506, a second side 508, a third side 510, and a fourth side 512. The dispenser carton 500 includes an open space 580 disposed between the four sides 506, 508, 510, 512 and the lower surface 504, into which contents can be inserted into the dispenser carton 500. The upper surface 502 can form a lid or closure for the open space 580 to close the dispenser carton 500 and enclose the contents therein. Optionally, as shown in FIG. 1, the dispenser carton 500 may include a dispenser label 590 affixed thereto, e.g., on the upper surface 502 thereof. The upper surface 502 include a closure flap 515 extending from one side thereof. The upper surface 502 may additionally include one or more side closure flaps, e.g., side closure flaps 514 and 516, extending therefrom. For instance, the closure flap 515 may extend from a side of the upper surface 502 coinciding with the third side 510 of the carton 500, and the side closure flaps 514 and 516 may extend from sides of the upper surface 502 coinciding with the second side 508 and fourth side 512 of the carton 500, respectively.

The closure flap 515 can be configured to overlap or cover the third panel 510 when the upper surface 502 of the dispenser carton 500 is closed. In this configuration, as shown in FIG. 15A-B, the first side closure flap 514 can be inserted into a first flap slot 520 and the second side closure flap 516 can be inserted into a second flap slot 522. The first flap slot 520 can be disposed along an edge between the third side 510 and the second side 508 of the dispenser carton 500. The second flap slot 522 can be disposed along an edge between the third side 510 and the fourth side 512 of the dispenser carton 500. The closure flap 515 can optionally include a closure tab 518, e.g. in a center of the closure flap 515, configured to be inserted into a closure tab slot 524. The closure tab slot 524 can be located on the third side 510 of the dispenser carton 500, or can be located along a junction between the third side 510 and the lower surface 504 of the dispenser carton 500. In other arrangements of the invention, one or more cooperating closure tabs 518 and closure tab slots 524 can be positioned around the dispenser carton 500 to provide additional means for securing the dispenser carton closed.

The dispenser carton 500 has a length 570 extending along the first side 506 and third side 510, a width 572 extending along the second side 508 and fourth side 512, and a height 574 extending from the upper surface 502 to the lower surface 504. The length 570 can be in a range from about 15 inches to about 20 inches, such as from about 15.5 inches to about 17 inches, for example, in one embodiment, the length 570 may be about 16.125 inches. The width 572 may be in a range from about 6 inches to about 9 inches, such as from about 7 inches to about 8 inches, for example, in one embodiment the width may be about 7.75 inches. As shown in FIGS. 15A and 15B, the height 574 of the dispenser carton 500 may vary depending on the intended contents of the dispenser carton 500. For instance, if the dispenser carton 500 is intended for a probe kit having one or two probes, the dispenser carton 500 has a height 574a. If the dispenser carton 500 is intended for a probe kit having three or four probes 20, the dispenser carton 500 has a height 574b that is greater than the height 574a. For example, the height 574a may be in a range from about 3 inches to about 4 inches, for example about 3.25 inches. The height 574b may be in a range from about 4 inches to about 5 inches, for example about 3.75 inches.

The dispenser carton 500 may additionally include a first bumper 530 and/or a second bumper 550 configured to provide additional protective packaging to the probe kit, i.e., the outer carrier tray 100 and its contents. In particular, the first bumper 530 and/or second bumper 550 can be configured to keep the flange 112 of the outer carrier tray 100 away from the walls or sides 506, 508, 510, 512 of the dispenser carton 500 such that the bumpers 530 and/or 550 may absorb impact during shipping and/or handling of the dispenser carton 500. The first bumper 530 can extend from and/or be attached to the fourth side 512 of the dispenser carton 500. The second bumper 550 can extend from and/or be attached to the second side 508 of the dispenser carton 500. Each of the bumpers 530, 550 may have a generally rectangular shape.

The first bumper 530 has a first side 532, a second side 534, a third side 536 and a fourth side 538. The first bumper 530 additionally has a front side 540 and a rear side 542, as shown in FIGS. 15A-B. The first side 532 is configured to be aligned with, e.g., coplanar with, the fourth side 512 of the dispenser carton 500. The second side 534 is configured to be aligned with, i.e., coplanar with, the upper surface 502 of the dispenser carton 500. The third side 536 is configured to extend parallel to the first side 532, and the fourth side 538 is configured to extend parallel to the second side 536. When the upper surface 502 of the dispenser carton 500 is closed over the open space 580, the front side 540 is configured to be aligned with, i.e., coplanar with and/or in contact with, the third side 510 of the dispenser carton 500, and the rear side 542 is configured to be aligned with, i.e., coplanar with and/or in contact with, the first side 506 of the dispenser carton 500. Moreover, when the upper surface 502 of the dispenser carton 500 is closed over the open space 580, the fourth side 538 of the bumper 530 is configured to be positioned in alignment with, e.g., coplanar with, in contact with and/or resting on, a surface of a dispenser insert 600, which is described in further detail below.

The second bumper 550 has a first side 552, a second side 554, a third side 556 and a fourth side 558. The first bumper 550 additionally has a front side 560 and a rear side 562, as shown in FIGS. 15A-B. The first side 552 is configured to be aligned with, e.g., coplanar with, the second side 508 of the dispenser carton 500. The second side 554 is configured to be aligned with, i.e., coplanar with, the upper surface 502 of the dispenser carton 500. The third side 556 is configured to extend parallel to the first side 552, and the fourth side 558 is configured to extend parallel to the second side 556. When the upper surface 502 of the dispenser carton 500 is closed over the open space 580, the front side 560 is configured to be aligned with, i.e., coplanar with and/or in contact with, the third side 510 of the dispenser carton 500, and the rear side 562 is configured to be aligned with, i.e., coplanar with and/or in contact with, the first side 506 of the dispenser carton 500. Moreover, when the upper surface 502 of the dispenser carton 500 is closed over the open space 580, the fourth side 558 of the bumper 550 is configured to be positioned in alignment with, e.g., coplanar with, in contact with and/or resting on, a surface of a dispenser insert 600, which is described in further detail below. In the described configuration, as illustrated in FIGS. 15A-B, the first bumper 530 and the second bumper 550 are arranged in a generally identical and/or mirrored configuration such that the first bumper 530 and the second bumper 550 can provide cushioning and/or stability to any contents of the dispenser carton 500 to prevent the contents from contacting the sides 508, 512 of the dispenser carton 500.

Figure 16:
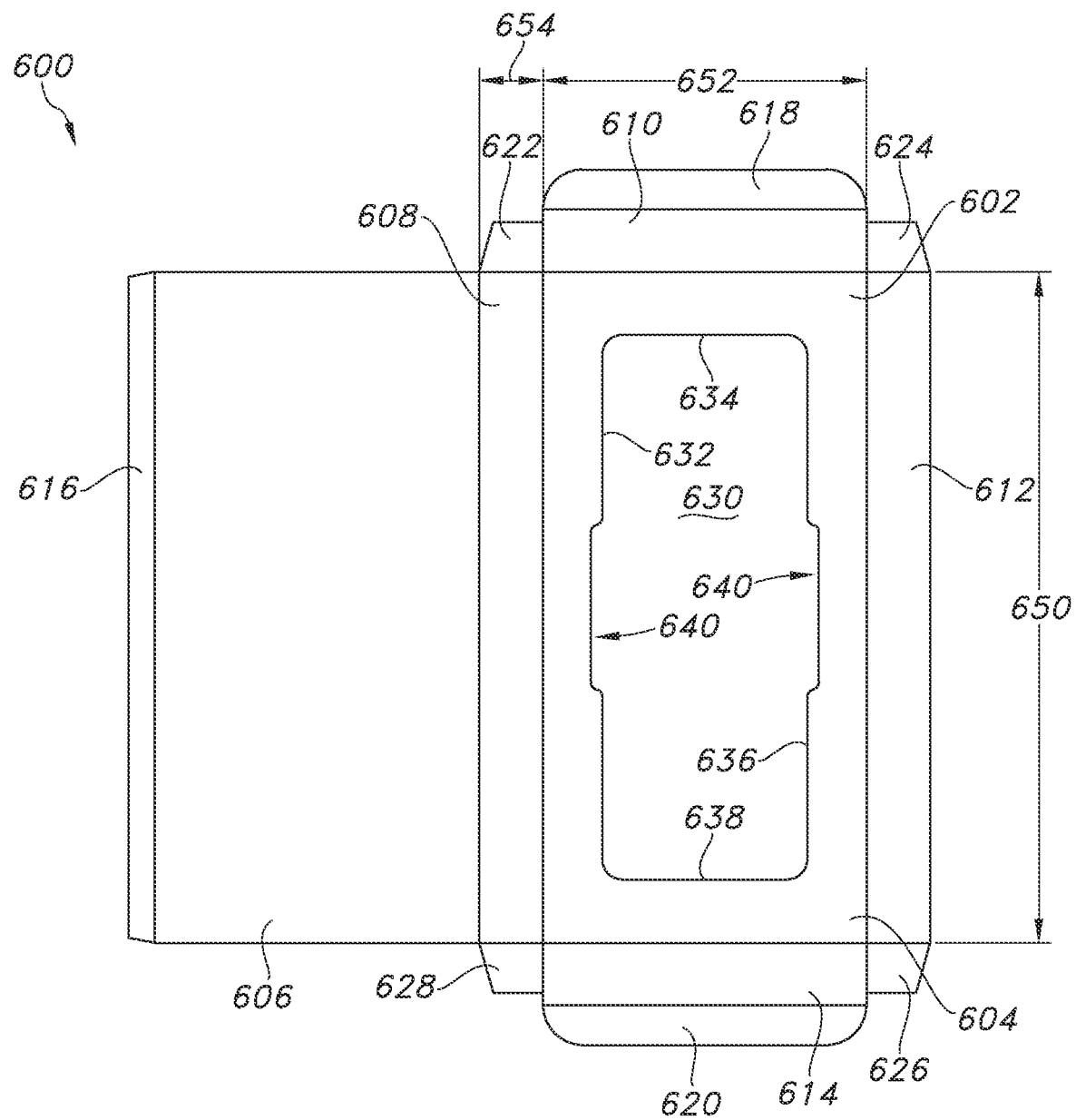
FIG. 16 illustrates a top view of a dispenser insert according to an embodiment of the present invention.

The dispenser carton 500 may further include a dispenser insert 600 inserted therein, as shown in FIGS. 15A-B and 16. Specifically, the dispenser insert 600 may be inserted into the open space 580 of the dispenser carton 500. The dispenser insert 600 can provide a stabile structure for an outer carrier tray 100 containing a probe kit to be contained within the dispenser carton 500 in order to minimize movement within the dispenser carton 500. The dispenser insert 600 is formed from a body 602 having an upper surface 604 and a lower surface 606, a first side 608 configured to be aligned with the first side 506 of the dispenser carton 500, a second side 610 configured to be aligned with the second side 508 of the dispenser carton 500, a third side 612 configured to be aligned with the third side 510 of the dispenser carton 500, and a fourth side 614 configured to be aligned with the fourth side 512 of the dispenser carton.

When folded along seams between the upper surface 604, lower surface 606, and the sides 608, 610, 612, 614, the dispenser insert 600 can form a generally rectangular shape or a box-shape. The lower surface 606 can have a connecting flap 616 extending therefrom. The connecting flap 616 can be configured to contact the third side 612 of the body 602 such that the dispenser insert forms a generally rectangular shape. In this configuration, as shown in FIGS. 15A-B, the lower surface 606 can extend below and generally parallel to the upper surface 604. The connecting flap 616 of the lower surface 606 may be secured to the third panel 612 using any suitable means, such as adhesive. The second side 610 can have a connecting flap 618 extending therefrom, and the fourth side 614 can have a connecting flap 620 extending therefrom, as shown in FIG. 16. The connecting flaps 618 and 620 can be configured to contact the lower surface 606 in order to further secure the dispenser insert 600 in a folded configuration substantially similar to an enclosed rectangle or box shape. The connecting flaps 618 and 620 may each be secured to the lower surface 606 using any suitable means, such as adhesive. In addition, the body 602 may have additional folding flaps 622, 624, 626 and 628 configured to support the dispenser insert 600 in the folded configuration. For instance, the folding flap 622 may extend from an end of the first side 608 adjacent to the second side 610, the folding flap 624 may extend from an end of the third side 612 adjacent to the second end 610, the folding flap 626 may extend from an end of the third side 612 adjacent to the fourth side 614, and the folding flap 628 may extend from the first side 608 adjacent to the fourth side 614. Each of the folding flaps 622, 624, 626, 628 may optionally be secured to their respective adjacent sides 610 or 614 by any suitable means, such as adhesive, or may be freely folded without any means of securing the flaps to other structures of the dispenser insert 600.

As shown in FIGS. 15A-B and 16, the dispenser insert 600 is configured to receive the outer carrier tray 100 therein. Specifically, the dispenser insert 600 includes an opening 630 within the upper surface 604. The opening 630 is defined by a first side 632 configured to be aligned with, e.g., parallel to, the first side 608 of the dispenser insert 600 and the first side 506 of the dispenser carton 500; a second side 634 configured to be aligned with, e.g., parallel to, the second side 610 of the dispenser insert 600 and the second side 508 of the dispenser carton 500; a third side 636 configured to be aligned with, e.g., parallel to, the third side 612 of the dispenser insert 600 and the third side 510 of the dispenser carton 500; and a fourth side 638 configured to be aligned with, e.g., parallel to, the fourth side 614 of the dispenser insert 600 and the fourth side 512 of the dispenser carton 500. The tray opening 630 can have a shape, i.e., length and width, generally equal to the length 130 and width 132 of the outer carrier tray 100 such that the outer carrier tray 100 can be nested therein. The tray opening 630 can further include at least one depression 640 along one or more of the sides 632, 634, 636, 638 that is configured to provide a gap between the opening 630 and the outer carrier tray 100 to assist a user in removing the outer carrier tray 100 from the dispenser carton 500. The dispenser insert 600 is configured to keep the flange 112 of the outer carrier tray 100 away from the walls or sides 506, 508, 510, 512 of the dispenser carton 500 such that the dispenser insert 600 may absorb any impact during shipping and/or handling of the dispenser carton 500. The dispenser insert 600 is thus intended to provide additional protective packaging to the probe kit(s).

The dispenser carton 500 and the dispenser insert 600 each may be constructed of any suitable packaging material including paper-based materials such as, for example, carton cardboard stock, paperboard, container stock, corrugated paperboard, plastic coated paper, a plastic sheet, or a combination thereof. The paper-based material(s) can be provided as a single layer or multiple layers. In some aspects of the invention, the dispenser carton 500 and the dispenser insert 600 are each formed from paperboard or fiberboard, in particular, solid bleached sulfate (SBS; also known as solid bleached board). The paper-based material(s) may have a thickness in a range from about 0.02 inches (about 0.5 mm) to about 0.04 inches (about 1 mm), for instance about 0.024 inches (about 0.6 mm).

The dispenser insert 600 has a length 650 extending along the first side 608 and third side 612, a width 652 extending along the second side 610 and the fourth side 614, and a height 654 configured to extend in a plane extending between the upper surface 604 and lower surface 604. The length 650 may be in a range from about 14 inches to about 18 inches, such as from about 15 inches to about 16 inches, for example, in one particular embodiment, the length 650 is about 15.625 inches. The width 652 may be in a range from about 5 inches to about 10 inches, such as from about 7 inches to about 9 inches, for example, in one particular embodiment, the width 650 is about 7.625 inches. The height 654 of the dispenser insert 600 may vary depending on the number of probes 20 in the probe kit inserted within the dispenser carton 500, i.e. includes a height 654*b* for a dispenser 500 for containing a probe kit including three or four probes 20 that is greater than a height 654*a* for dispenser 500 for containing a probe kit including one or two probes 20, as shown in FIGS. 15A-B. For instance, the height 654*a* may be in a range from about 0.5 inches to about 1.5 inches, such as about 1 inch. The height 654*b* may be in a range from about 2 inches to about 4 inches, for example about 2.875 inches.

Figure 17:
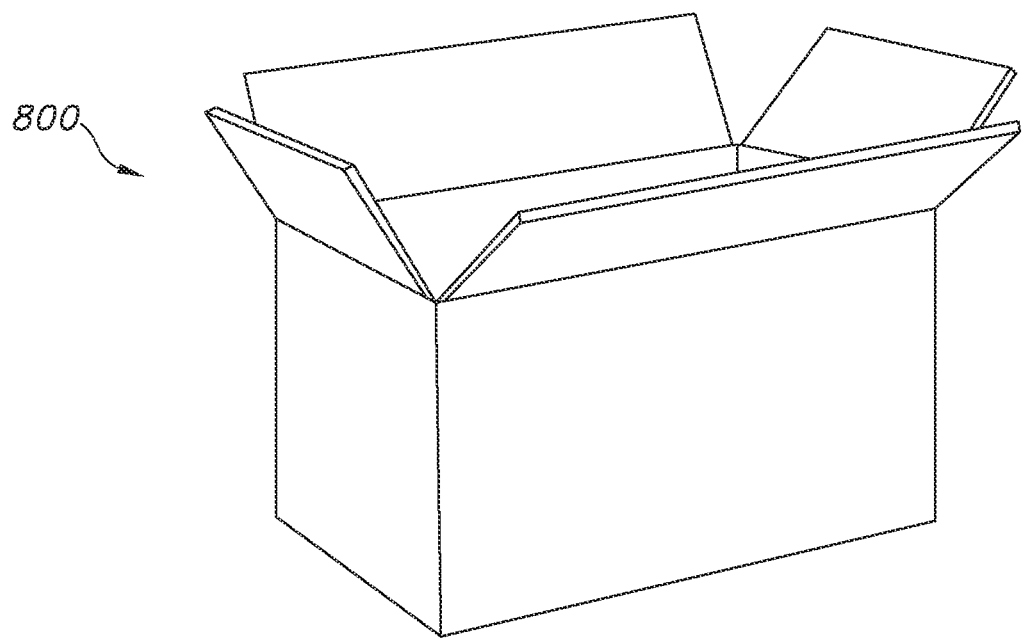
FIG. 17 illustrates a perspective view of a shipping case according to an embodiment of the present invention.

The present invention may further include a shipping carton 800, as shown in FIG. 17. The shipping carton 800 may be in the form of a knocked down flat (KDF) corrugate carton. For instance, the shipping carton 800 may be a shipping case comprised of C flute craft corrugate, or any other suitable shipping case. One or more dispenser cartons 500 may fit within the shipping carton 800.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A system for packaging a kit for a radiofrequency ablation procedure, the system comprising:
   an introducer tray having at least one introducer-shaped indentation formed therein for receiving at least one introducer;
   a probe tray having at least one probe assembly-shaped indentation formed therein for receiving at least one radiofrequency ablation probe assembly, the at least one radiofrequency ablation probe assembly comprising a radiofrequency ablation probe attached to a probe handle and a cable/tubing that extends from the probe handle;
   a probe sleeve configured to surround the at least one radiofrequency ablation probe assembly within the probe tray to facilitate a secure fit of the at least one radiofrequency ablation probe assembly within the probe tray, the probe sleeve formed from a single piece of material folded into a rectangular shape;
   an outer carrier tray, wherein the introducer tray and the probe tray are held within the outer carrier tray;
   a pouch configured to hold a tubing kit; and
   a dispenser carton, wherein the outer carrier tray and the pouch are configured to be held within the dispenser carton.

2. The system of claim 1, wherein the introducer tray is configured to nest within the probe tray.

3. The system of claim 1, further comprising a second probe tray configured to hold at least a second radiofrequency ablation probe assembly.

4. The system of claim 3, wherein the at least one radiofrequency ablation probe assembly comprises two radiofrequency ablation probe assemblies.

5. The system of claim 3, wherein the second probe tray is configured to stack with the probe tray.

6. The system of claim 3, wherein the introducer tray is configured to nest within the probe tray or the second probe tray.

7. The system of claim 1, wherein the outer carrier tray comprises a lid formed from high density polyethylene fibers, wherein the lid is configured to seal the outer carrier tray to form a sterile barrier.

8. The system of claim 7, wherein the contents of the outer carrier tray are configured to be terminally sterilized after the outer carrier tray is sealed by the lid.

9. The system of claim 1, wherein the pouch comprises a first material comprising high density polyethylene and a second material comprising a low density polyethylene film.

10. The system of claim 9, wherein the pouch is sealed, further wherein the contents of the pouch are configured to be terminally sterilized after the pouch is sealed.

11. The system of claim 1, wherein the dispenser carton comprises a dispenser carton insert configured to minimize movement of the outer carrier tray and the pouch within the dispenser carton.

12. The system of claim 1, further comprising a case configured to hold a plurality of dispenser cartons, wherein the case is formed from knocked-down flat (KDF) corrugate material.

13. The system of claim 1, wherein the dispenser carton is made from paperboard.

14. The system of claim 1, wherein the probe tray, the introducer tray, and the outer carrier tray are each thermoformed trays.

15. The system of claim 14, wherein the thermoformed trays are formed from polyethylene terephthalate glycol.

16. The system of claim 1, wherein the single piece of material that forms the probe sleeve is paperboard.

17. The system of claim 1, the introducer tray further comprising four sides, each of the four sides comprising one or more indented portions to facilitate gripping of the introducer tray, wherein opposite sides of the four sides mirror each other with respect to the one or more indented portions.

18. The system of claim 17, wherein one or more sides of the outer carrier tray have a depression formed therein to facilitate removal of the introducer tray and the probe tray from the outer carrier tray, wherein the one or more depressions are aligned with the one or more indented portions of the introducer tray.

19. The system of claim 1, the probe tray further comprising four sides, at least two sides each having an indented portion formed thereon, wherein the indented portions are formed at a central portion of the probe tray to facilitate gripping of the probe tray.

20. The system of claim 1, wherein the at least one probe assembly-shaped indentation comprises a probe-shaped indentation formed along an edge of the probe tray and a cable/tubing indentation formed near a center of the probe tray.

* * * * *